(12) United States Patent
Ngadi et al.

(10) Patent No.: US 12,416,617 B2
(45) Date of Patent: Sep. 16, 2025

(54) SYSTEM AND METHOD OF EGG FERTILITY AND GENDER DETECTION

(71) Applicant: MATRIXSPEC SOLUTIONS INC., Baie d'Urfe (CA)

(72) Inventors: Michael Ngadi, Pierrefonds (CA); Li Liu, Sainte-Anne-de-Bellevue (CA)

(73) Assignee: MATRIXSPEC SOLUTIONS INC., Baie d'Urfe (CA)

( * ) Notice: Subject to any disclaimer, the term of this patent is extended or adjusted under 35 U.S.C. 154(b) by 129 days.

(21) Appl. No.: 18/266,506

(22) PCT Filed: Dec. 10, 2021

(86) PCT No.: PCT/CA2021/051779
§ 371 (c)(1),
(2) Date: Jun. 9, 2023

(87) PCT Pub. No.: WO2022/120491
PCT Pub. Date: Jun. 16, 2022

(65) Prior Publication Data
US 2024/0044860 A1    Feb. 8, 2024

Related U.S. Application Data

(60) Provisional application No. 63/124,114, filed on Dec. 11, 2020.

(51) Int. Cl.
*G01N 33/08* (2006.01)
*G01N 21/47* (2006.01)
*G01N 21/49* (2006.01)

(52) U.S. Cl.
CPC .............. *G01N 33/08* (2013.01); *G01N 21/49* (2013.01); *G01N 2021/4704* (2013.01)

(58) Field of Classification Search
CPC ...... G01N 33/08; G01N 33/085; G01N 21/49; G01N 21/47; G01N 21/00; G01N 21/01;
(Continued)

(56) References Cited

U.S. PATENT DOCUMENTS

| 5,615,777 A | 4/1997 | Weichman |
| 9,686,969 B2 | 6/2017 | Meissner |

(Continued)

FOREIGN PATENT DOCUMENTS

| CA | 2804903 A1 | 12/2010 |
| CN | 214041128 U | 8/2021 |

(Continued)

OTHER PUBLICATIONS

Plonus, Martin. 7.1.2 Digital Signals in an Analog World (pp. 236-237). Butterworth-Heinemann (Year: 2020).*

(Continued)

*Primary Examiner* — Hina F Ayub
*Assistant Examiner* — Christina I Xing
(74) *Attorney, Agent, or Firm* — Bennett Jones LLP; Lorelei G. Graham

(57) ABSTRACT

An egg analysis system and computer-implemented methods are provided. The system comprises a light source for illuminating an egg, a photon detector for detecting a fluctuation of scattering light emitted from the egg, a processor, and a memory storing instructions which when executed by the processor configure the processor to receive scattering light data from the photon detector, digitize the scattering light data, and analyze the digitized scattering light data. One computer-implemented method comprises a light source illuminating an egg, a photon detector detecting a fluctuation of scattering light emitted from the egg, receiving scattering light data from the photon detector, digitizing the scattering light data, and analyzing the scattering light (Continued)

data. Another computer-implemented method comprises receiving angle, frequency and intensity data of scattering light from an egg illuminated using a light source, identifying a germinal disc in the egg from the scattering light data, and determining at least one of a fertility or a sex of the egg based on the size and structure of the germinal disc.

18 Claims, 5 Drawing Sheets

(58) Field of Classification Search
CPC ... G01N 2021/4704; G01N 2021/4707; G01N 2021/4711; G01N 2021/4714; G01N 2021/4721; G01N 2021/4723; G01N 2021/4716; G01N 2021/4719; A01K 43/00; A01K 43/06
See application file for complete search history.

(56) References Cited

U.S. PATENT DOCUMENTS

| | | | |
|---|---|---|---|
| 10,015,952 B2 * | 7/2018 | Adar | A01K 41/00 |
| 10,222,260 B2 | 3/2019 | McQuilkin | |
| 10,607,338 B2 | 3/2020 | Ngadi | |
| 10,705,066 B2 * | 7/2020 | Green | G01N 21/31 |
| 10,713,782 B2 | 7/2020 | Ngadi | |
| 11,302,000 B2 | 4/2022 | Ngadi | |
| 11,688,064 B2 | 6/2023 | Ngadi | |
| 2002/0075476 A1 | 6/2002 | Chalker | |
| 2002/0157613 A1 | 10/2002 | Phelps | |
| 2003/0172392 A1 | 9/2003 | Mendu | |
| 2008/0283449 A1 | 11/2008 | Madsen | |
| 2009/0038557 A1 * | 2/2009 | Meter | A01K 41/06 119/300 |
| 2013/0044210 A1 | 2/2013 | Rozenboim | |
| 2016/0069743 A1 | 3/2016 | McQuilkin | |
| 2016/0100557 A1 | 4/2016 | Adar | |
| 2016/0239953 A1 | 8/2016 | Ngadi | |
| 2018/0033139 A1 | 2/2018 | Ngadi | |
| 2019/0159433 A1 | 5/2019 | Feinberg | |
| 2019/0174726 A1 | 6/2019 | Knepper | |
| 2019/0195689 A1 | 6/2019 | McQuilkin | |
| 2019/0339244 A1 * | 11/2019 | Steiner | A01K 43/00 |
| 2019/0383782 A1 | 12/2019 | Steiner | |
| 2020/0088580 A1 | 3/2020 | Darty | |
| 2020/0110068 A1 | 4/2020 | Green | |
| 2020/0281166 A1 | 9/2020 | Haase | |
| 2020/0302604 A1 | 9/2020 | Ngadi | |
| 2020/0400640 A1 | 12/2020 | Preusse | |
| 2022/0230313 A1 | 7/2022 | Ngadi | |
| 2023/0281812 A1 | 9/2023 | Ngadi | |

FOREIGN PATENT DOCUMENTS

| | | |
|---|---|---|
| EP | 2890973 B1 | 8/2020 |
| HK | 1225226 A | 9/2017 |
| KR | 10-2018-0055970 A | 5/2018 |
| TR | 202016317 T4 | 10/2020 |

OTHER PUBLICATIONS

Liu et al., "Detecting Fertility and Early Embryo Development of Chicken Eggs Using Near-Infrared Hyperspectral Imaging", Sep. 2012 (Year: 2012).

International Search Report + Written Opinion issued for PCT/CA2023/050329 on May 24, 2023.

* cited by examiner

SYSTEM AND METHOD OF EGG FERTILITY AND GENDER DETECTION

CROSS REFERENCE TO RELATED APPLICATIONS

This application is a national stage entry of PCT/CA2021/051779 filed Dec. 10, 2021, which claims the benefit of and priority to U.S. provisional application No. 63/124,114 filed Dec. 11, 2020, the contents of all of which are hereby incorporated by reference.

FIELD

The present disclosure generally relates to systems and methods of detecting egg fertility and gender.

INTRODUCTION

Fertility and hatchability of eggs are critical economic factors for hatcheries and poultry breeding farms. Only about 60 to 90% of incubated eggs are fertile and eventually hatch in commercial hatcheries. Non-hatching eggs include infertile eggs or fertile eggs where the embryos have died. Infertile eggs may comprise up to 25% of all eggs set. These eggs may be useful for commercial egg tables or low grade food stock.

The sex of fertile eggs is also among the egg characteristics of interest for the poultry industry. In the layer egg industry, chicks are sexed at hatch and the female birds (that will lay eggs) are considered paramount while the male birds are culled. The opposite is the case with the broiler industry in which the male species are crucial. In either case, discarding of the unwanted chicks creates serious bottlenecks as far as waste disposal and animal welfare issues are concerned.

SUMMARY

In accordance with an aspect, there is provided an egg analysis system. The system comprises a laser for illuminating an egg, a photon detector for detecting a fluctuation of scattered light emitted from the egg, a processor, and a memory storing instructions which when executed by the processor configure the processor to receive scattered light data from the photon detector, digitize the scattered light data, and analyze the digitized scattered light data.

In some embodiments, the egg analysis system comprises at least one of an imaging subsystem comprising the light source, a detection subsystem comprising the photon detector, or an actuating subsystem.

In accordance with another aspect, there is provided a computer-implemented method of analyzing an egg. The computer-implemented method comprises a light source illuminating an egg, a photon detector detecting a fluctuation of scattered light emitted from the egg, receiving scattering light data from the photon detector, digitizing the scattering light data, and analyzing the scattering light data.

In accordance with another aspect, there is provided a computer-implemented method of determining fertility and sex of eggs. The computer-implemented method comprises receiving angle, frequency and intensity data of scattering light from an egg illuminated using a light source, identifying a germinal disc in the egg from the scattering light data, and determining at least one of a fertility or a sex of the egg based on the size and structure of the germinal disc In accordance with another aspect, there is provided a computer-implemented method of determining fertility and sex of eggs. The computer-implemented method comprises receiving angle, frequency and intensity data of scattered light from an egg illuminated using a laser, measuring the scattering light data to determine a size and molecular weight of a germinal disc of the egg, determining an average scatter size of the germinal disc, determining a structure of the germinal disc, and determining a fertility and a sex of the egg based on the size and structure of the germinal disc.

In various further aspects, the disclosure provides corresponding systems and devices, and logic structures such as machine-executable coded instruction sets for implementing such systems, devices, and methods.

In this respect, before explaining at least one embodiment in detail, it is to be understood that the embodiments are not limited in application to the details of construction and to the arrangements of the components set forth in the following description or illustrated in the drawings. Also, it is to be understood that the phraseology and terminology employed herein are for the purpose of description and should not be regarded as limiting.

Many further features and combinations thereof concerning embodiments described herein will appear to those skilled in the art following a reading of the instant disclosure.

DESCRIPTION OF THE FIGURES

Embodiments will be described, by way of example only, with reference to the attached figures, wherein in the figures.

It is understood that throughout the description and figures, like features are identified by like reference numerals.

DETAILED DESCRIPTION

Embodiments of methods, systems, and apparatus are described through reference to the drawings. Applicant notes that the described embodiments and examples are illustrative and non-limiting. Practical implementation of the features may incorporate a combination of some or all of the aspects, and features described herein should not be taken as indications of future or existing product plans.

In some embodiments, in order to identify and isolate infertile eggs and separate female and male eggs, in-ovo fertility and gender determination processes have been developed using Hyperspectral Imaging and Machine Learning technologies. The processes were developed based on statistical methods and have shown very promising results on egg fertility and gender determination prior to incubation.

In some embodiments, in-ovo fertility and gender determination techniques have been developed based on light scattering patterns through the pre-incubated eggs. The scattered light patterns were then analyzed using statistical methods in order to determine the egg fertility and gender of the eggs.

In some embodiments, 'distinguishing features' in the obtained hyperspectral images and/or light scattering patterns have been identified that can consistently differentiate non-fertile eggs from fertile eggs, and male eggs from female eggs.

Figure 1A:
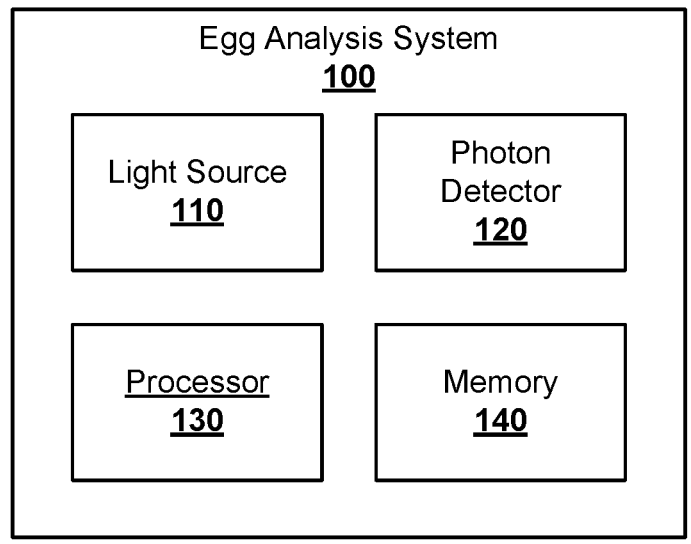
FIG. 1A illustrates, in a component diagram, an example of a system for analyzing eggs, in accordance with some embodiments.

FIG. 1A illustrates, in a component diagram, an example of a system for analyzing eggs 100, in accordance with some embodiments. The system 100 comprises a light source (e.g., a laser) 110, and at least one photon detector 120. In some embodiments, eggs may be illuminated by a laser 110 beam (or other light source beam), and the fluctuations of the scattered light detected at a known scattering angle θ by a fast photon detector 120. Cells in the eggs scatter the light from the laser 110 beam, and the imprint information is detected by the photon detector 120 and used in an analysis that yields information about the cellular particles. The intensity fluctuations of the incident beam is characterized by computing the intensity correlation function, whose analysis provides the diffusion coefficient of the particles (also known as diffusion constant). Since particles of different sizes scatter with different intensities, different scattering angles may be examined in order to determine the optimum angle of detection for the eggs. Other components may be added to the system 100, including a processor 130 and a memory 140 storing instructions to digitize and analyze the imprint information. For example, the memory 140 may include a digitization module and an analysis module.

Figure 1B:
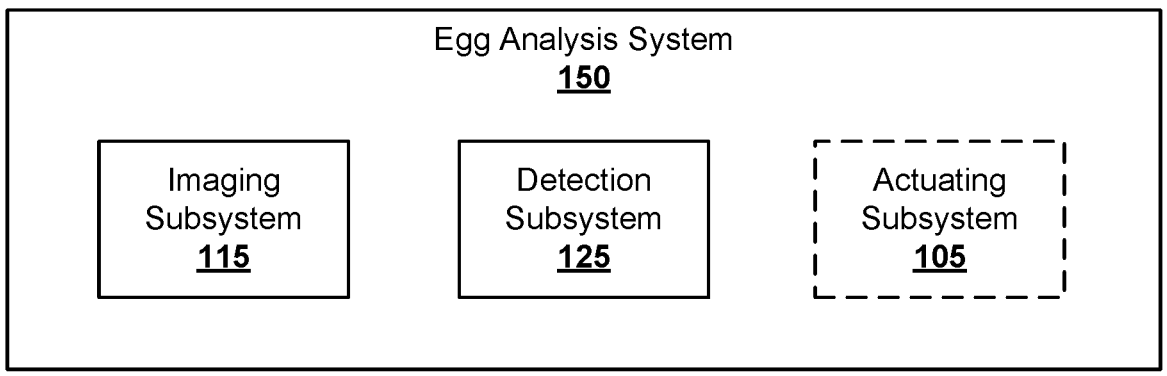
FIG. 1B illustrates, in a component diagram, another example of a system for analyzing eggs in accordance with some embodiments.

FIG. 1B illustrates, in a component diagram, another example of a system for analyzing eggs 150, in accordance with some embodiments. The system 150 includes an imaging subsystem 115, a detection subsystem 125, and optionally an actuating subsystem 105. In some embodiments, the actuating subsystem 105 may be external to the system 150. The subsystems 115, 125 and 105 may have separate processors 130 and memory 140, or alternatively may share a common system 150 processor 130 and memory 140.

In some embodiments, the light source is part of an imaging subsystem 115 that includes a line-scan spectrograph interconnected with an InGaAs camera configured to capture images (e.g., spectral images, scattered light). In one example implementation, the spectrograph is a Hyperspec™ spectrograph provided by Headwall Photonics Inc. (USA) with a near-infrared spectral range spanning approximately 900 nm to 1700 nm and a spectral resolution of 2.8 nm. In an embodiment, image data is collected in transmission mode. In an embodiment, image data is collected and processed at 100 frames per second. In an embodiment, the imaging system may include a wide field, area scan, snapshot camera.

In some embodiments, one or more light sources 110 in the imaging subsystem 115 may be used to provide back illumination for an egg to facilitate image capture of the fluctuations of scattered light. In one example implementation, a single 250-watt quartz tungsten halogen lamp is used as a light source.

In some embodiments, the photon detector 120 is part of a detection subsystem 125 that analyses received scattering data to detect cellular particles in an egg, including, for example, a germinal disc.

In some embodiments, system 100 may optionally include an actuating system 105 to actuate a conveyor configured to move an egg into the field of view of the system's photon detector 120 (e.g., camera) optics. In one example implementation, the conveyor is a Dorner 2200 series conveyer provided by Dorner Mfg. Corp. (USA), driven by a MDIP22314 stepping motor provided by Intelligent Motion System Inc. (USA). The speed of the conveyor may be adjustable. For example, the speed of the conveyor may be adjusted based on the speed of the photon detector 120 (e.g., camera optics) to minimize image distortion (e.g., motion blur). The speed of the conveyor may also be adjusted based on other factors, e.g., desired detection throughput.

The conveyor may include trays or racks adapted to receive eggs therein. In some embodiments, the trays or rack may then be stored (either on or off the conveyor) while maintaining each egg in a given position (e.g., a vertical position, a first angled position, a second angled position, etc.). In some embodiments, the rack may rotate such that the eggs therein are maintained in a different positon (e.g., a vertical position, a first angled position, a second angled position, etc.).

In an embodiment, the conveyor may be configured to present multiple eggs (e.g., two eggs, four eggs, etc.) to be imaged simultaneously. Accordingly, in this embodiment, each spectral image or scattering data may include data for multiple eggs, and each such image or scattering data may be segmented during processing to isolate scattering data for each egg. Processor 130 may be configured to send control commands to conveyor to control its movement.

The imaging subsystem 115 may be interconnected with a detection subsystem 125 by way of a conventional serial or parallel interface. In an embodiment, imaging subsystem 115 may be interconnected with detection subsystem 125 by way of a network comprising wired links, wireless links, or a combination thereof. In this embodiment, one or both of imaging subsystem 115 and detection subsystem 125 may include a suitable network interface and/or network transceivers. In some embodiments, the detection subsystem 125 may be a cloud service which receives scattering data for an egg as input, and provides a sex and/or fertility of the egg as output.

In some embodiments, the detection subsystem 125 or system 100 may connect to an actuating subsystem 105 to trigger actuation of apparatuses based on results computed by the detection subsystem 125. The actuating subsystem 105 is operable to transmit a control signal to actuate an apparatus according to the classified unhatched egg. The actuating subsystem 105 is operable to generate data signals for the gender and fertility of the unhatched egg, for example. The actuating subsystem 100 is operable to transmit the output data signals to hardware or apparatus to trigger actuation thereof. For example, the actuating subsystem 105 may move or separate the unhatched egg.

In some embodiments, an actuating subsystem 105 may receive data signals of classification results from the detection subsystem 125 and removes the undesired eggs (non-fertile and/or male) from the assembly line using one or more apparatuses that are in physical contact with the eggs or otherwise can trigger movement or separation of eggs. For example, actuating subsystem 105 may include or interface with one or more robotic arms with end effectors (robotic hands) that may be used to grasp and drop or replace eggs which are indicated by the classification signals from detection subsystem as non-fertile and/or male eggs. There may be other apparatuses that can separate or move eggs based on the classification signals from detection subsystem and this is an illustrative example only. Accordingly, the actuating subsystem 105 triggers actuation of hardware components based on the classification signals from detection subsystem 125. In example embodiments the actuation may involve physical movement of the eggs to separate the eggs into different streams, for example. As another example a conveyer may be triggered or controlled to move eggs. Detection subsystem 125 generates output signals for actuating subsystem 105 to provide control commands to trigger actuation of various apparatuses.

Figure 2:
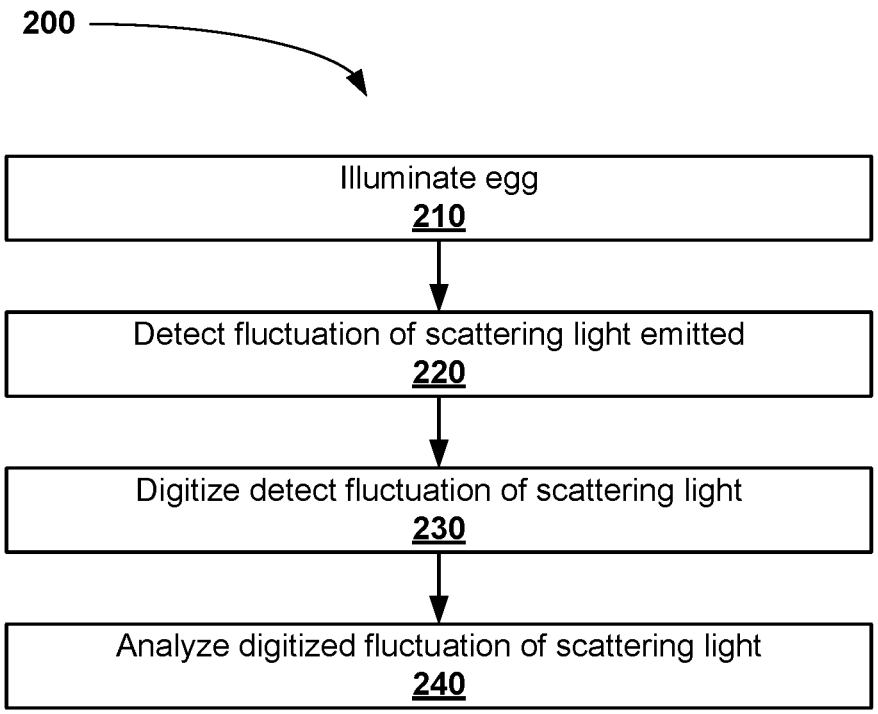
FIG. 2 illustrates, in a flowchart, an example of a method of analyzing eggs, in accordance with some embodiments.

FIG. 2 illustrates, in a flowchart, an example of a method of analyzing eggs 200, in accordance with some embodiments. The method 200 comprises illuminating 210 an egg using a light source (e.g., a laser) 110 beam, and detecting 220 fluctuations of scattered light emitting from the egg using a fast photon detector 120. Next the fluctuations, or imprint information, detected by the photon detector 120 is digitized 230, and the digitized information analysed 240 for cellular particulars. For example, an intensity correlation function may be performed to determine the diffusion coefficients of the particles (i.e., diffusion constant). Other steps may be performed by the method 200, including determining an optimal angle of detection for the egg.

The shape and size of the germinal disc which floats on the egg yolk is different between fertile and non-fertile eggs. The germinal disc in a fertile egg (also called blastoderm) is visually seen as a symmetrical circular ring, while the germinal disc in a non-fertile egg (also called blastodisc) looks like an asymmetrical solid spot. There have been several studies to identify possible gender differentiating features prior to incubation. It is known that there could be about 40,000 to 60,000 blastoderm cells available in the germinal disc of chicken egg. Female birds are heterogametic with one Z and one W sex chromosome, whereas male birds have two Z chromosomes. The Z chromosome has approximately threefold higher DNA content than the W chromosome. Therefore, the total DNA amount in cells from male birds will be higher than in cells from female birds.

Application of multivariate methods for spectral feature selection has produced promising results in such fields as tumor identification or classification of different cell types. Further, considering that the germinal disc of the male egg is denser than that of the female egg, the spectral scattering patterns are expected to be different and could explain the statistical difference observed by the spectral and image features extracted from the hyperspectral images. Therefore, the distinguishing features for fertility and gender detection may be discovered based on light scattering measurement.

Light scattering happens when light "hits" a small object (a particle or a molecule) and thereby changes its direction. It is a process when incident light of energy is absorbed by an object and subsequently light of energy is emitted. The angle, frequency and intensity (i.e. power) of light scattering can be measured to determine the size and the molecular weight of materials. Angle-resolved scattering measurements capture light as a function of the scattering angle, and invert the angles to deduce the average size of the scattering objects via a computational light scattering model such as Mie scattering theory, which predicts angles based on the size of the scattering sphere. Combining these techniques allows for a measurement of average scatter size of the object. In addition, multiple scattering properties that can be calculated by averages of single sphere scattering efficiencies obtained from Mie scattering theory are also used to predict the structure of the object. Therefore, egg fertility and gender detection methods have been developed based on the predicted size and structure of germinal disc using different light scattering measurements and patterns.

As noted above, in some embodiments, prediction of egg fertility and gender of non-incubated eggs is based on identifying and characterizing light scattering patterns of the egg's germinal disc (or other cells in mitochondrial DNA). Therefore, the germinal disc should be in the camera's field of view (FOV) during scanning. Eggs may be scanned with its "big" (i.e., large) end upwards. The "big" or "large" end is considered to be the larger in diameter of the two ends of an egg. What is desired is to ensure that the germinal disc is located on top of the big/large end of the egg in order to appropriately record and measure its light scattering patterns. Normally the germinal disc in the egg could be located randomly anywhere on the surface of the egg's yolk. In some embodiments, a protocol of egg handling provides that the germinal disc is located on top of the egg (big/large end) and in the camera's field of view.

Figure 3:
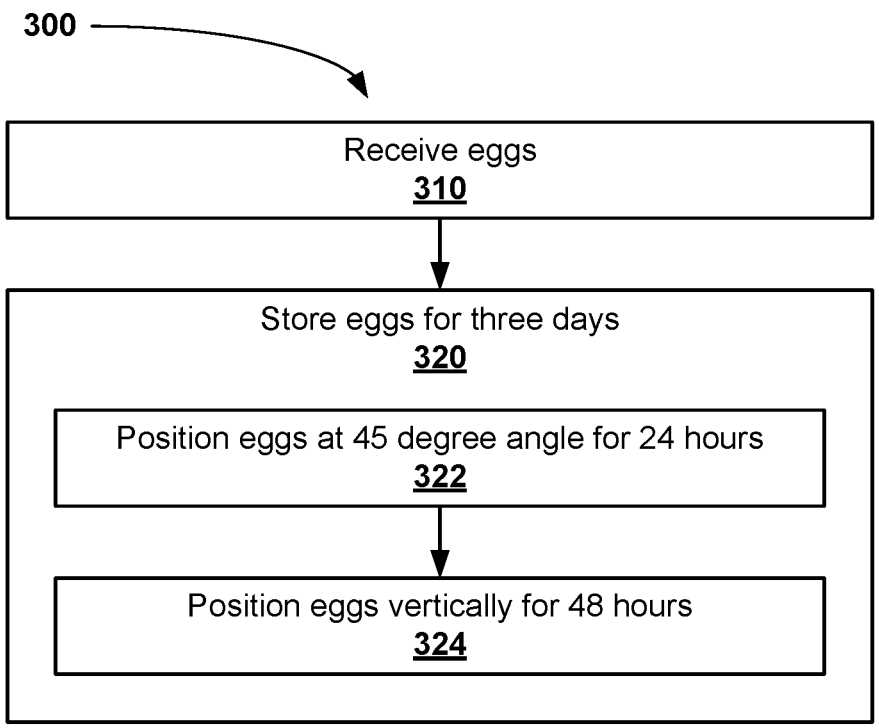
FIG. 3 illustrates, in a flowchart, an example of a protocol (e.g., method) of handling an egg such that its germinal disc is located on the top (large end) of the egg, in accordance with some embodiments.
Figure 4B:
FIG. 4B illustrates an example of eggs positioned in a vertical position, in accordance with some embodiments.
Figure 4A:
FIG. 4A illustrates an example of eggs positioned at 45 degree angle, in accordance with some embodiments.

FIG. 3 illustrates, in a flowchart, an example of a protocol (e.g., method) of handling an egg such that its germinal disc is located on the top (large end) of the egg 300, in accordance with some embodiments. The method 300 may be performed by an egg processing system. Eggs may be placed in a tray 310 with their big end upwards. For example, an egg processing system may be configured to receive eggs in a manner that causes the eggs to fall into place in a rack of an egg holding apparatus. Next, the eggs may be stored 320 at approximately between 18 to 20 degrees Celsius for at least three days. The eggs (e.g., the rack holding the eggs) may be positioned 322 at a first angle (e.g., approximately a 45 degree angle) for a first period (e.g., the first approximately 24 hours). For example, an actuator of an egg processing system may rotate the rack at approximately a 45 degree angle. FIG. 4A illustrates an example of eggs positioned at 45 degree angle 400, in accordance with some embodiments. Next the eggs (e.g., the rack holding the eggs) are positioned 324 at a second angle (e.g., flat; the rack may be in a horizontal positon such that the eggs are in a vertical position with the "big" end up") for a second period (e.g., the next approximately 48 hours). For example, a timer may indicate that the rack has been at approximately 45 degrees for a first time period (e.g., approximately 24 hours) which triggers the actuator to rotate the rack to a horizontal (flat) position. Alternatively, the racks may be set to rotate at pre-determined times. It should be understood that the eggs may be left in the approximately 45 degree angle for longer than 24 hours and then in the vertical position (i.e., flat rack) for longer than 48 hours. Alternatively, the rack or tray may hold the eggs at a desired first angle when the rack or tray is flat, and then be rotated to an angel such that the eggs are then in a vertical position in the rack or tray. Other, angles for racks and trays may be used. FIG. 4B illustrates an example of eggs positioned in a vertical position 450, in accordance with some embodiments. At this point, the germinal disc should be located at the top (large end) of the egg.

An experiment was conducted to investigate the effectiveness of this protocol 300 on the germinal disc location in an egg. A total of 100 freshly laid fertile eggs were received from a local egg farm over the course of a month. Upon arrival the eggs were stored for three days. Fifty eggs were stored according to the protocol, while the remaining 50 eggs were stored only in the vertical direction with the big end up at the same room temperature for three days. After the three-day storage, the eggshell of each egg was carefully peeled from the center of the egg top (large end) to the side of the boundary defined by the camera's FOV to assess the location of the corresponding germinal disc. For the eggs that were stored as per the protocol, 43 out of 44 eggs (98%) showed the germinal disc right on top of the eggs upon opening and examining the eggs. For the eggs that were stored for three days without positioning at 45 degrees, 38 out of 43 eggs (88%) had their germinal disc on top of the eggs. Thus, the experiment showed that the likelihood of locating germinal disc on top of the egg and in the camera's FOV can be increased by applying the egg handling protocol 300. Therefore, the protocol 300 may improve the performance of egg fertility and gender detection methods that are developed based on detection of light scattering characteristics of the germinal disc.

Figure 5:
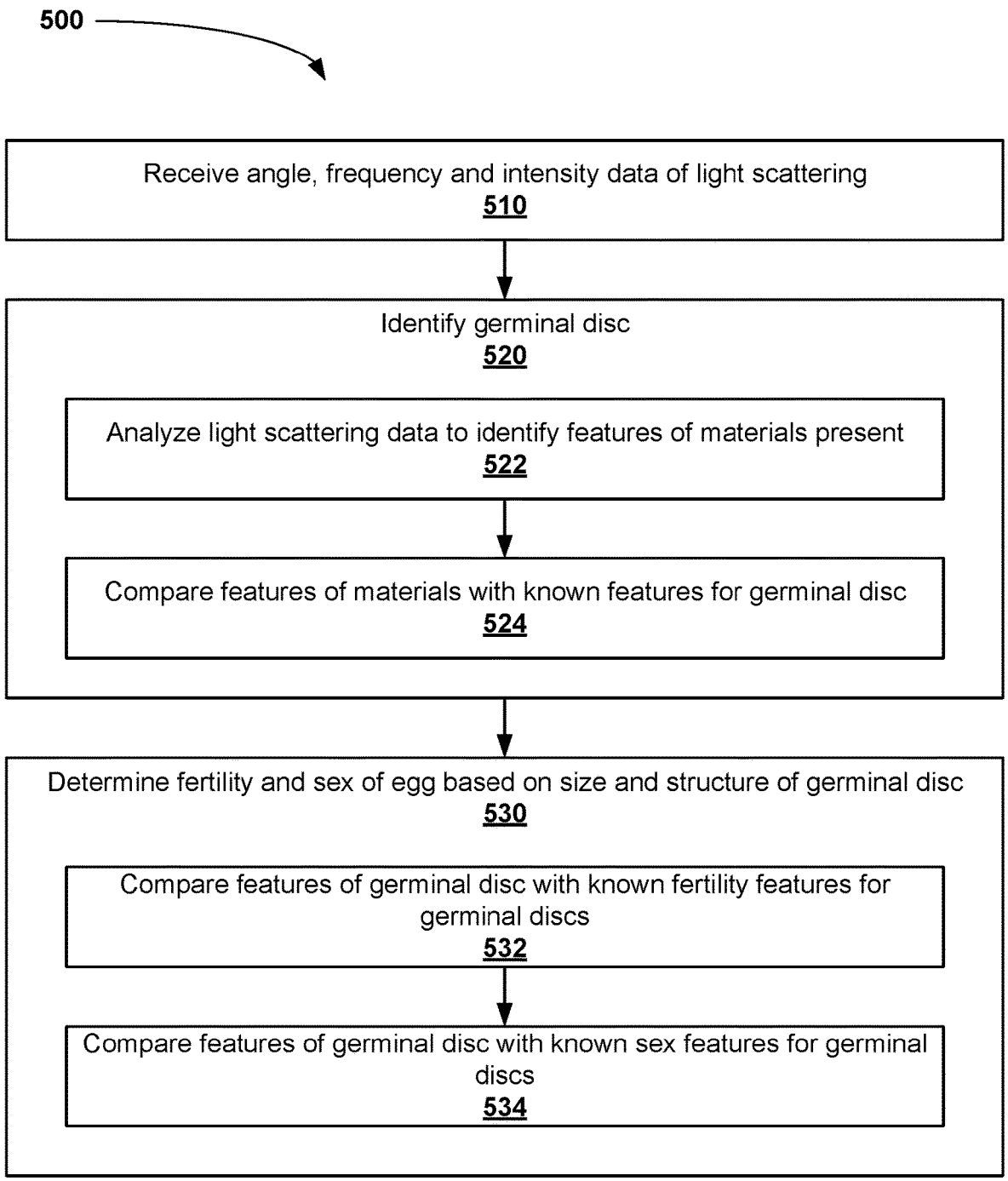
FIG. 5 illustrates, in a flowchart, an example of a method of analyzing light scattering, in accordance with some embodiments.

FIG. 5 illustrates, in a flowchart, an example of a method of analyzing light scattering 500, in accordance with some embodiments. The method comprises receiving 510 angle, frequency and intensity data of light scattering obtained from a photon detector 120 from an egg illuminated using a light source 110. For example, eggs may be placed in an egg holder and on a conveyor. The light source 110 may be positioned to align with the photon detector 120 (e.g., HSI camera). The light source 110 will illuminate the egg at the small end, while the big/large end of the egg will be in the FOV of the photon detector. The light scattering data may then be analyzed 520 to identify the germinal disc. The light scattering data is analyzed 522 to identify features of materials present. Next, features (e.g., size, shape, orientation, etc.) of each material in the light scattering data is compared 524 with known features of germinal discs to identify the germinal disc in the light scattering data from any other material or particle present. Next, the fertility and/or sex of the egg is determined 530 based on the size and structure of the identified germinal disc. Features of the identified germinal disc are compared 532 with known fertility features for germinal discs. For example, in a non-fertile egg, the scattering image data of the germinal disc egg may show features that are related to blastodisc which looks like a white pimple; while in a fertile egg, the scattering image data of the germinal disc may show features that are related to blastoderm which looks like a white hollow disc with a white pimple at the centre. Similarly, features of the identified germinal disc are compared 534 with known sex features for germinal discs. Thus, the identified germinal disc data is compared to known germinal disc features to distinguish between fertile and non-fertile eggs, and between male and female eggs. Other steps may be added to the method, including following germinal disc placement protocol 300, and separating distinguished eggs based on egg type using a conveyor subsystem.

Figure 6:
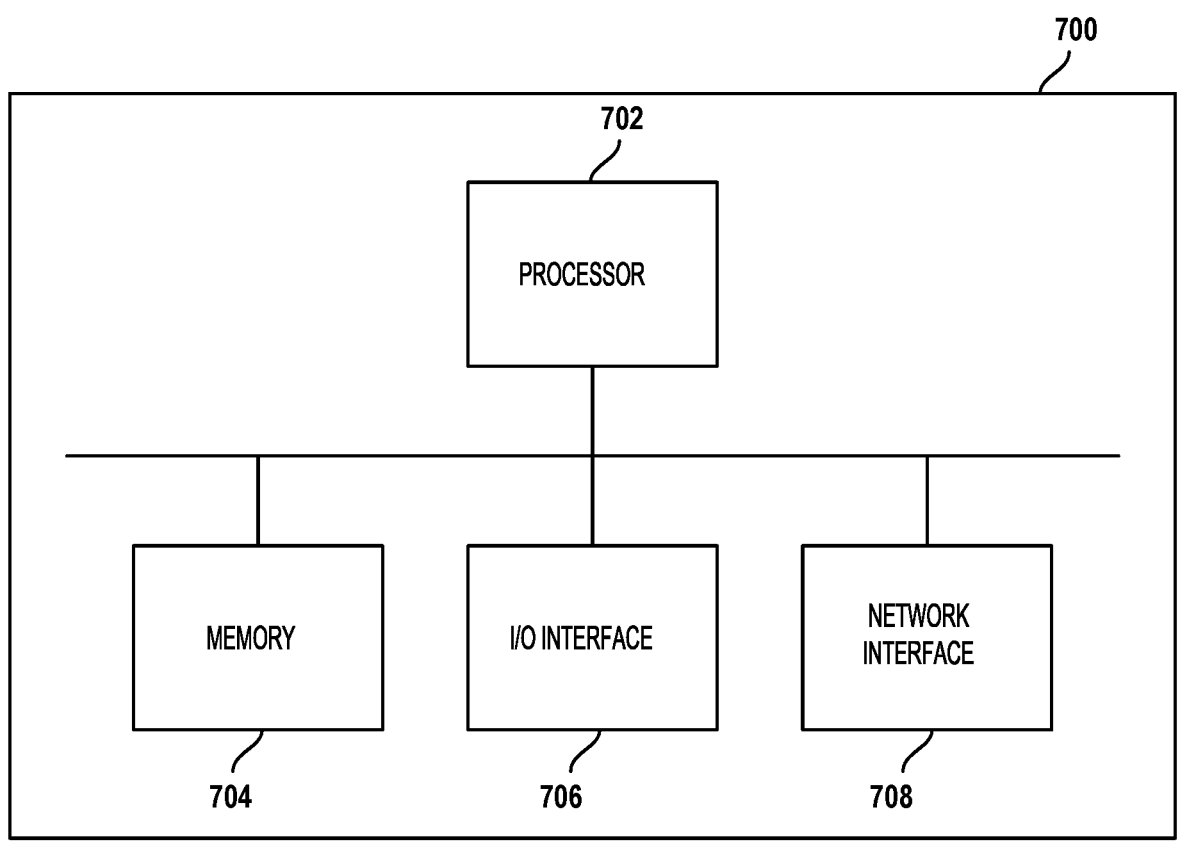
FIG. 6 is a schematic diagram of a computing device such as a server or other computer in a device.

FIG. 6 is a schematic diagram of a computing device 700 such as a server or other computer in a device. As depicted, the computing device includes at least one processor 702, memory 704, at least one I/O interface 706, and at least one network interface 708.

Processor 702 may be an Intel or AMD x86 or x64, PowerPC, ARM processor, or the like. Memory 704 may include a suitable combination of computer memory that is located either internally or externally such as, for example, random-access memory (RAM), read-only memory (ROM), compact disc read-only memory (CDROM).

Each I/O interface 706 enables computing device 700 to interconnect with one or more input devices, such as a keyboard, mouse, camera, touch screen and a microphone, or with one or more output devices such as a display screen and a speaker.

Each network interface 708 enables computing device 700 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others.

The foregoing discussion provides example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements.

Although the embodiments have been described in detail, it should be understood that various changes, substitutions and alterations can be made herein.

Moreover, the scope of the present application is not intended to be limited to the particular embodiments of the process, machine, manufacture, composition of matter, means, methods and steps described in the specification.

As can be understood, the examples described above and illustrated are intended to be exemplary only.

What is claimed is:

1. An egg analysis system comprising:
    a light source for illuminating one end of an egg;
    a photon detector for detecting a fluctuation of scattering light emitted from an approximate opposite end of the egg;
    a tray configured to hold one or more eggs at different angles;
    a timer configured to track a time that the tray is at a specific angle;
    at least one processor; and
    a memory storing instructions which, when executed by the processor, configure the at least one processor to:
        actuate the tray to position itself at a first angle for a first period of time, said tray holding the egg such that a large end of the egg higher than a small end of the egg;
        responsive to the timer indicating that the tray has been in the first angle for the first period of time, actuate the tray to position the egg in a vertical position with the large end up for a second period of time;
        responsive to the timer indicating that the tray has been in the second angle for the second period of time, actuate the light source to illuminate the egg;
        receive scattering light data from the photon detector;
        digitize the scattering light data; and
        analyze the digitized scattering light data.

2. The egg analysis system as claimed in claim 1, comprising at least one of:
    an imaging subsystem comprising the light source;
    a detection subsystem comprising the photon detector; or
    an actuating subsystem.

3. The system as claimed in claim 1, wherein the at least one processor is configured to:
    receive angle, frequency and intensity data of the scattering light;
    identify a germinal disc of the egg; and
    determine at least one of a fertility or a sex of the egg based on the size and structure of the germinal disc.

4. The system as claimed in claim 3, wherein to identify the germinal disc of the egg, the at least one processor is configured to:
    analyze light scattering data to identify features of material present; and
    compare the identified features of material present with known features for germinal discs.

5. The system as claimed in claim 3, wherein to determine the fertility of the egg, the at least one processor is configured to compare features of the identified germinal disc with known fertility features for germinal discs.

6. The system as claimed in claim 5, wherein the at least one processor is configured to actuate a conveyor based on the fertility of the egg.

7. The system as claimed in claim 3, wherein to determine the sex of the egg, the at least one processor is configured to compare features of the identified germinal disc with known sex features for germinal discs.

8. The system as claimed in claim 7, wherein the at least one processor is configured to actuate a conveyor based on the sex of the egg.

9. The system as claimed in claim 1, wherein at least one of:
    the first angle is approximately 45 degrees;
    the first period is approximately 24 hours; or
    the second period is approximately 48 hours.

10. A computer-implemented method of analyzing eggs, the method comprising:
    actuating a tray holding and egg to position itself at a first angle for a first period of time, said tray holding the egg such that a large end of the egg higher than a small end of the egg;
    responsive to a timer indicating that the tray has been in the first angle for the first period of time, actuating the tray to position the egg in a vertical position with the large end up for a second period of time;
    responsive to the timer indicating that the tray has been in the second angle for the second period of time, actuating a light source illuminating one end of an egg;
    detecting, at a photon detector, a fluctuation of scattering light emitted from an approximate opposite end of the egg;
    receiving scattering light data from the photon detector;
    digitizing the scattering light data; and
    analyzing the digitized scattering light data.

11. The computer-implemented method as claimed in claim 10, comprising:
    receiving angle, frequency and intensity data of the scattering light;
    identifying a germinal disc of the egg; and
    determining at least one of a fertility or a sex of the egg based on the size and structure of the germinal disc.

12. The computer-implemented method as claimed in claim 11, wherein to identify the germinal disc of the egg, the method comprises:
    analyzing light scattering data to identify features of material present; and
    comparing the identified features of material present with known features for germinal discs.

13. The computer-implemented method as claimed in claim 11, wherein to determine the fertility of the egg, the method comprises comparing features of the identified germinal disc with known fertility features for germinal discs.

14. The computer-implemented method as claimed in claim 13, comprising actuating a conveyor based on the fertility of the egg.

15. The computer-implemented method as claimed in claim 11, wherein to determine the sex of the egg, the method comprises comparing features of the identified germinal disc with known sex features for germinal discs.

16. The computer-implemented method as claimed in claim 15, comprising actuating a conveyor based on the sex of the egg.

17. The computer-implemented method as claimed in claim 10, wherein the first angle is approximately 45 degrees.

18. The computer-implemented method as claimed in claim 10, wherein at least one of:
    the first period is approximately 24 hours; or
    the second period is approximately 48 hours.

* * * * *